US00PP14522P39

(12) United States Plant Patent
Moore

(10) Patent No.: US PP14,522 P3
(45) Date of Patent: Feb. 10, 2004

(54) RASPBERRY CULTIVAR NAMED WSU 1090

(50) Latin Name: *Rubus ideaus L.*
Varietal Denomination: WSU 1090

(75) Inventor: Patrick P. Moore, Puyallup, WA (US)

(73) Assignee: Washington State University Research Foundation, Pullman, WA (US)

( * ) Notice: Subject to any disclaimer, the term of this patent is extended or adjusted under 35 U.S.C. 154(b) by 0 days.

(21) Appl. No.: 10/155,671

(22) Filed: May 24, 2002

(65) Prior Publication Data

US 2003/0229929 P1 Dec. 11, 2003

(51) Int. Cl.[7] ..... A01H 5/00

(52) U.S. Cl. ..... Plt./204

(58) Field of Search ..... Plt./204

*Primary Examiner*—Bruce R. Campell
*Assistant Examiner*—Susan B. McCormick
(74) *Attorney, Agent, or Firm*—Schwegman, Lundberg, Woessner & Kluth, P.A.

(57) ABSTRACT

A new and distinct cultivar of red raspberry (i.e., *Rubus idaeus* L. ) is provided. The cultivar, designated WSU 1090, forms exceptionally large fruit with good flavor. The fruit is conical in shape. The fruit is larger, firmer, and has a greater length / width ratio than the fruit of most raspberry cultivars.

5 Drawing Sheets

GOVERNMENT INTERESTS

The invention was made in part with Federal formula funds pursuant to the Hatch Act and was part of Project WNP00640. The United States Government has certain rights in the invention.

FIELD OF THE INVENTION

This invention concerns a new and distinct cultivar of red raspberry plant with a botanical name of *Rubus ideaus* L. The designation of the instant plant is WSU 1090.

BACKGROUND OF THE INVENTION

Many cultivars of raspberry plant are known. For instance, raspberry cultivars named 'Emily,' 'Prelude,' and 'Holyoke' are described in U.S. Plant Pat. Nos. 12,350, 11,747, and 11,094 respectively. The parents of the new and distinct cultivar of the present invention are 'Chilliwack' and WSU 994. Other known raspberry cultivars include 'Tulameen' and 'Meeker'.

The instant plant, WSU 1090, originated from a hand-pollinated cross of 'Chilliwack' (non-patented)×WSU 994 (non-patented) made in 1989 at Washington State University Puyallup Research and Extension Center, Puyallup Wash. 'Chilliwack' is a red raspberry cultivar released from Agriculture and AgriFood Canada in 1987 that is not patented. 'Chilliwack' is a vigorous plant with erect laterals and produces firm fruit that releases easily from the receptacle. WSU 994 is a red raspberry selection from the Washington State University breeding program and is not patented. WSU 994 has long fruiting laterals and produces fruit with many drupelets per fruit. The fruiting laterals of WSU 994 are not stiff enough given their length and the fruit is soft.

SUMMARY OF THE INVENTION

WSU 1090 is distinguished primarily by its large, firm fruit. The fruit is attractive, with excellent traditional raspberry flavor. The fruit also has a greater length / width ratio than the fruit of most raspberry cultivars.

WSU 1090 is distinguished from its parent WSU 994 in having stiffer fruiting laterals, fruit that releases more easily from its receptacles, firmer fruit, and larger fruit.

WSU 1090 is distinguished from its parent 'Chilliwack' in having larger fruit, more drupelets per fruit, and a larger length / width ratio of its fruit.

WSU 1090 is distinguished from 'Meeker' in having thicker floricanes, wider and longer leaflets, fewer flowers per lateral, a more acidic fruit, firmer and larger fruit, and a larger length / width ratio of its fruit.

WSU 1090 is distinguished from 'Tulameen' in having longer and thicker floricanes and primocanes, wider and longer leaflets, longer laterals, larger and firmer fruit, and more drupelets per fruit.

BRIEF DESCRIPTION OF THE DRAWINGS

The accompanying photographs show typical specimens of the new cultivar, in color as nearly true as it is reasonably possible to make in color illustrations of this character. Photographs are intended to show morphological features of the plant.

DETAILED DESCRIPTION

History and Growth

Figure 1:
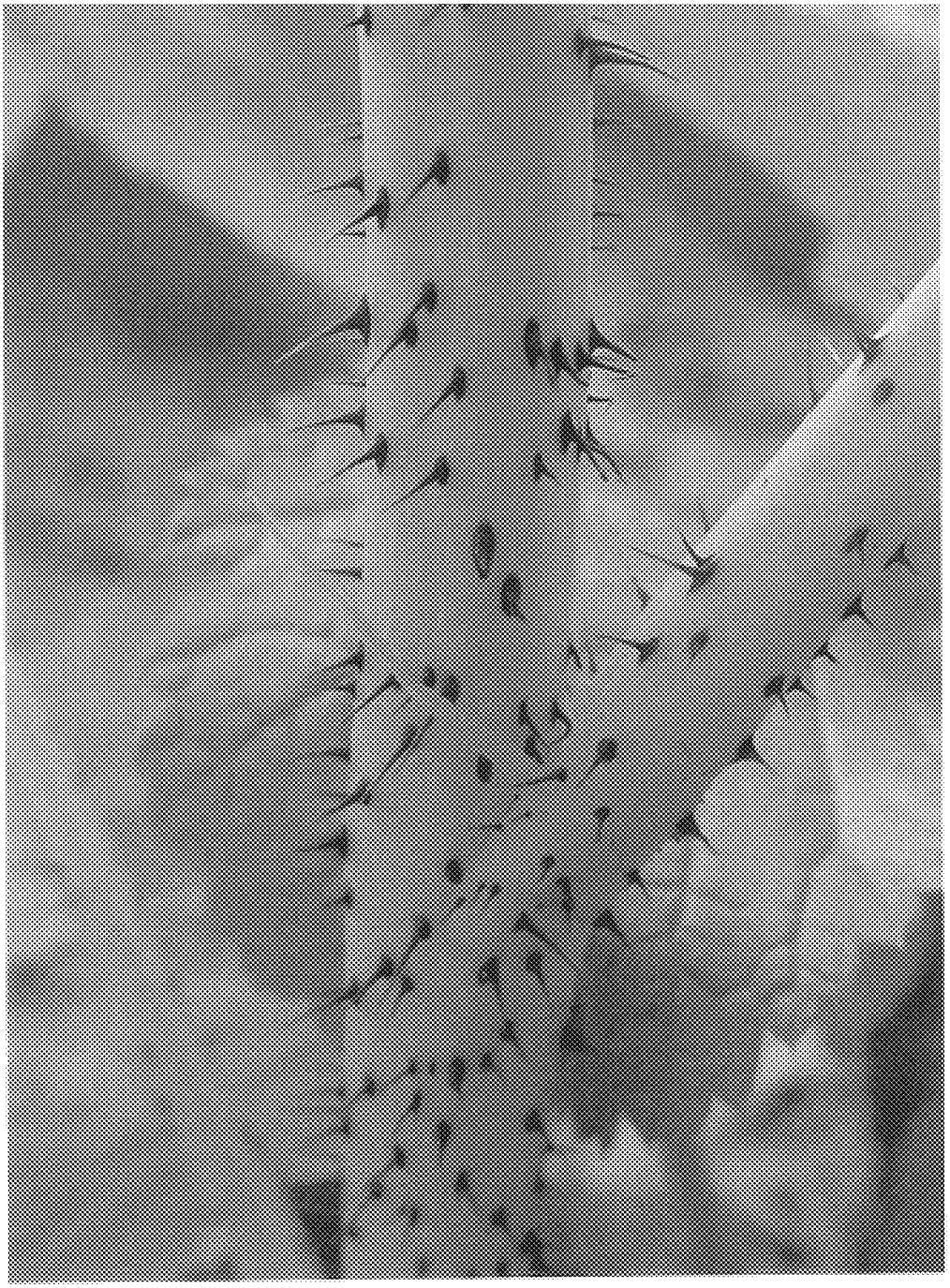
FIG. 1 is a photograph of a young primocane of WSU 1090, less than 30 cm tall, taken Jul. 20, 2001, showing frequency and shape of spines.

The seeds resulting from the controlled hybridization of 'Chilliwack'×WSU 994 were germinated in a greenhouse during the winter of 1989–1990. Resulting seedlings were planted in the spring of 1990 at Washington State University Puyallup Research and Extension Center, Puyallup, Wash. The seedlings fruited in 1992 and one, designated WSU 1090, was selected for its large, firm, attractive fruit and its apparent productivity.

During 1992, the original plant selection was propagated asexually in a greenhouse at Puyallup, Wash., by rooting cuttings derived from root material. A replicated planting of four replications of three plants each was established in spring 1993 at Puyallup, Wash. Subsequently, additional test plantings were established from asexually propagated plants that were propagated from root cuttings or micropropagated using meristem cultures from axillary buds of primocanes. Plantings were established in several locations in Washington (Vancouver; Puyallup; Mt. Vernon; and Lynden, Wash.). All asexually propagated plants have been observed to be true to type during all asexual multiplication and the vegetative and fruit characteristics of the original plants have been maintained. Plants fruited in the second or third season of growth after planting.

Test plantings have shown this new variety to be adapted to all tested locations in western Washington. There has been no observed winter damage, but winter hardiness is unknown.

Plants of the new variety have vigorous growth with long fruiting laterals. Plants have been grown in the hill system with 10–12 canes retained per hill and the primocanes pruned to 120 cm in winter. Fruiting plots were 213 cm tall with a width of 158 cm. An adequate number of canes have been produced each year.

Measurements

When objects could be accurately measured with an 8 mm diameter measuring opening (leaves and fruit), color was measured with a Minolta Chroma Meter CR-200b, which measures color in L*, a*, b* color coordinates. Calibration was performed using a standard white plate supplied by the manufacturer. These L*, a* , b* coordinates were converted and presented in Munsell color notation. For all other color measurements, color was compared with The Royal Horticultural Society Colour Chart color plates and presented as The Royal Horticultural Society Colour Chart designations (1966, published by The Royal Horticultural Society London and the Flower Council of Holland).

The descriptions reported herein are from specimens grown at Puyallup, Wash., unless otherwise noted.

Size

The number of canes per hill, diameter, cane length, number of nodes, internode length, and color are given in comparison to 'Meeker' (non-patented) and 'Tulameen' in Table 1. WSU 1090 produces an adequate number of canes and is very vigorous. The plant is similar in size to 'Meeker', which is noted as a large, vigorous cultivar with long fruiting laterals. Plants have been grown in the hill system with 10–12 canes retained per hill and the primocanes pruned to 1.2 m in winter. The following summer, fruiting plots were 213 cm tall with a width of 158 cm.

Canes

Figure 2:
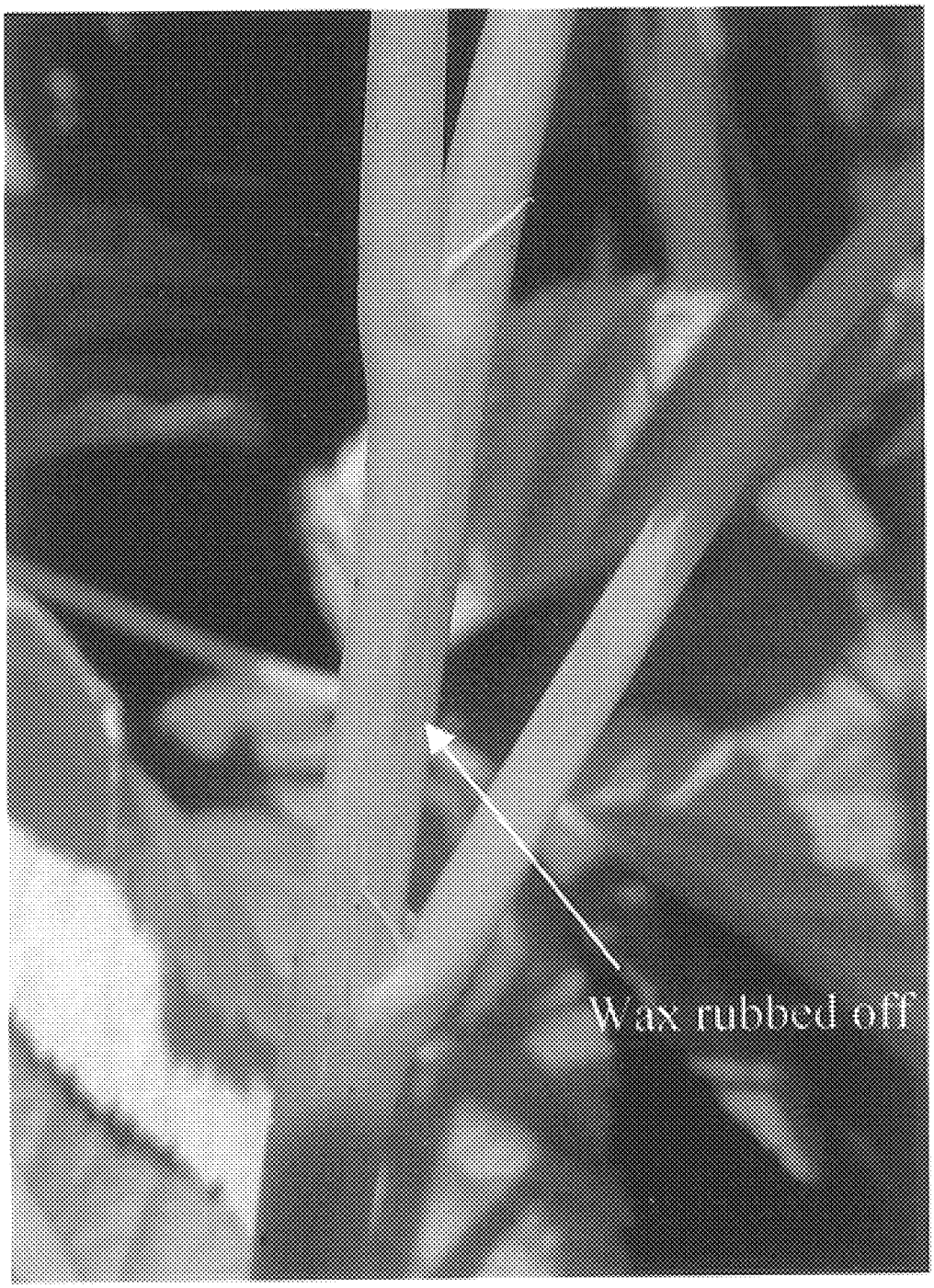
FIG. 2 is a photograph of a primocane of WSU 1090, approximately 1 m tall, taken Aug. 2, 2001 showing reduced numbers and size of spines. The waxy bloom is rubbed off in one portion of the cane.

Primocane emergence was similar for WSU 1090, 'Meeker' and 'Tulameen' and occurred approximately Mar. 20, 2001. Bud break for WSU 1090 was Mar. 9, 2001 and for 'Tulameen' Feb. 20, 2001 and for 'Meeker' Mar. 20, 2001. The cane color measured Mar. 20, 2001 was Grayed Orange group (175B) and the color of the bud scales were Grayed Purple group (183A). In midsummer Jul. 24, 2001) the cane color was much greener, Yellow-Green group (145B). Canes that are less than 30 cm tall have 20–40 spines per cm of cane (FIG. 1). At 1 m, the spines were much smaller and many fewer, less than 5 spines per cm (FIG. 2). The spine color is Red-Purple Group (71A). The spines are straight and pointed toward the base of the canes. There are pigmented spots at the base of the spine that are the same color as the spines. The spine color is similar to 'Tulameen' and much darker than 'Meeker'. The canes are glabrous, and they have a coating of wax (FIG. 2). The coating of wax on the canes occasionally forms blobs or wax accumulations that, without sufficient magnification, could be misinterpreted as pubescence.

Leaves

There is very sparse pubescence on the upper surface of the leaves with a greater density at the leaf margin. The leaflets are generally flat in cross-section. The petioles are pubescent and also have spines that are similar (but smaller) to those on the canes. These spines are visible in FIG. 1.

Figure 3:
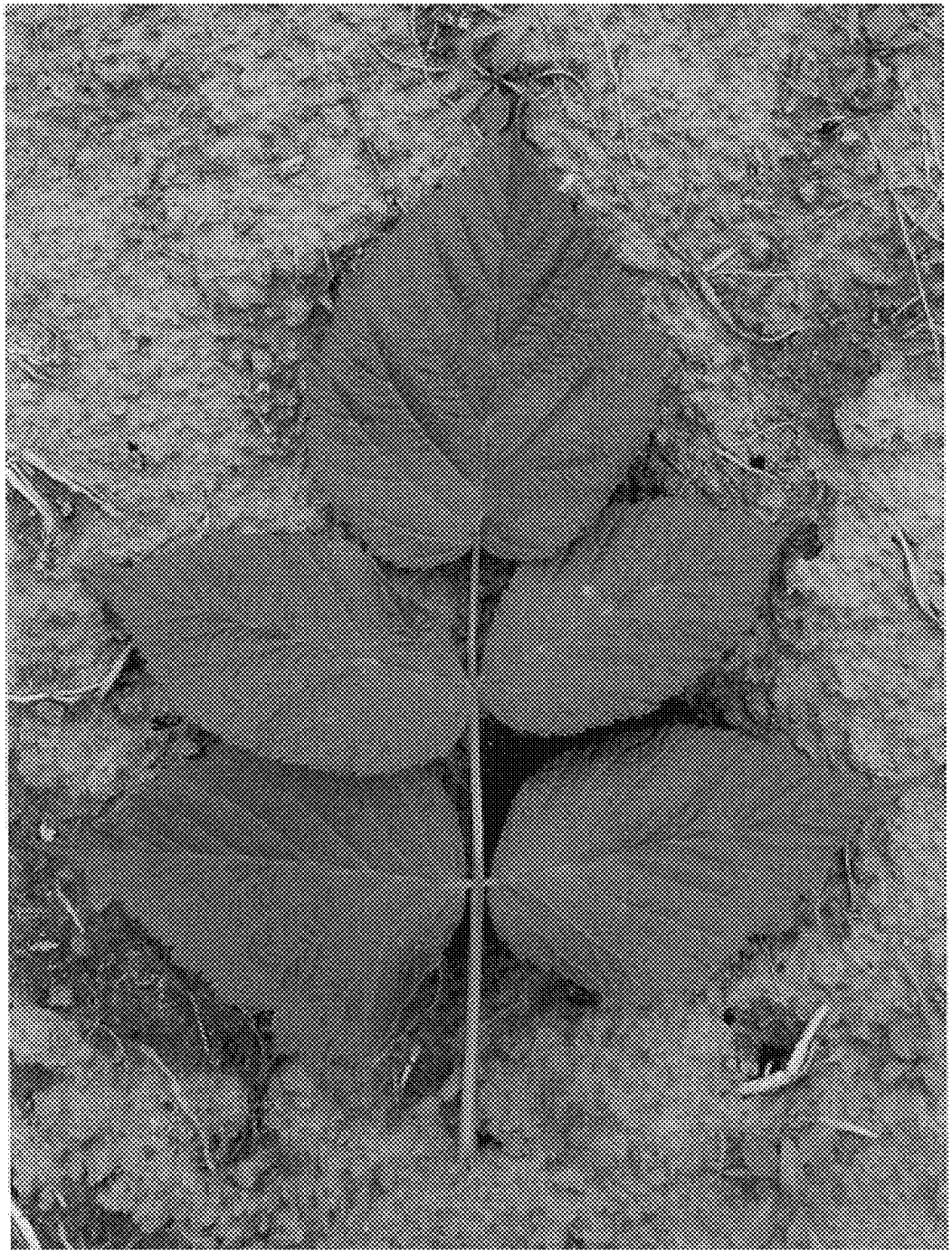
FIG. 3 is a photograph of the upper surface of a leaf from a primocane of WSU 1090.

Characteristics of primocane leaves are given in Table 2. The primocane leaves are pinnately compound with 5 leaflets (FIG. 3). Emerging leaves are green with some reddening. The leaves have 2 stipules. The basal lateral leaflets and the distal lateral leaflets overlap slightly. The leaflets are doubly serrated. The leaflets are generally ovate. The tips of all leaflets are acuminate to acute. The base of the terminal leaflet is rounded to cordate. The bases of the basal lateral leaflets are rounded and relatively symmetrical. The distal lateral leaflets are sessile with asymmetrical leaf bases.

Characteristics of floricane leaves are given in Table 3. The floricane leaves have 3 leaflets that do not overlap. The leaves have 2 stipules. The leaflets are generally ovate. The leaflet tips are acuminate to acute. The leaf bases for the terminal leaflet is cordate and the lateral leaflets are rounded.

Flowers and Fruit

Fruit of this variety ripens late in the season, with the midpoint of harvest averaging July 16 and the length of the fruiting season averaging 24 days at Puyallup, Wash. The midpoint of harvest for 'Tulameen' (non-patented) averaged July 14 with 28 days for the length of the fruiting season. Fruit production has not been observed on primocanes. Fruit releases easily from the receptacle. Fruit quality is maintained well in cold storage. The fruit is very large, averaging 5.0 g over the season. Early in the fruiting season, fruit was much larger, averaging 8.4 g on Jul. 6, 2001.

Figure 4:
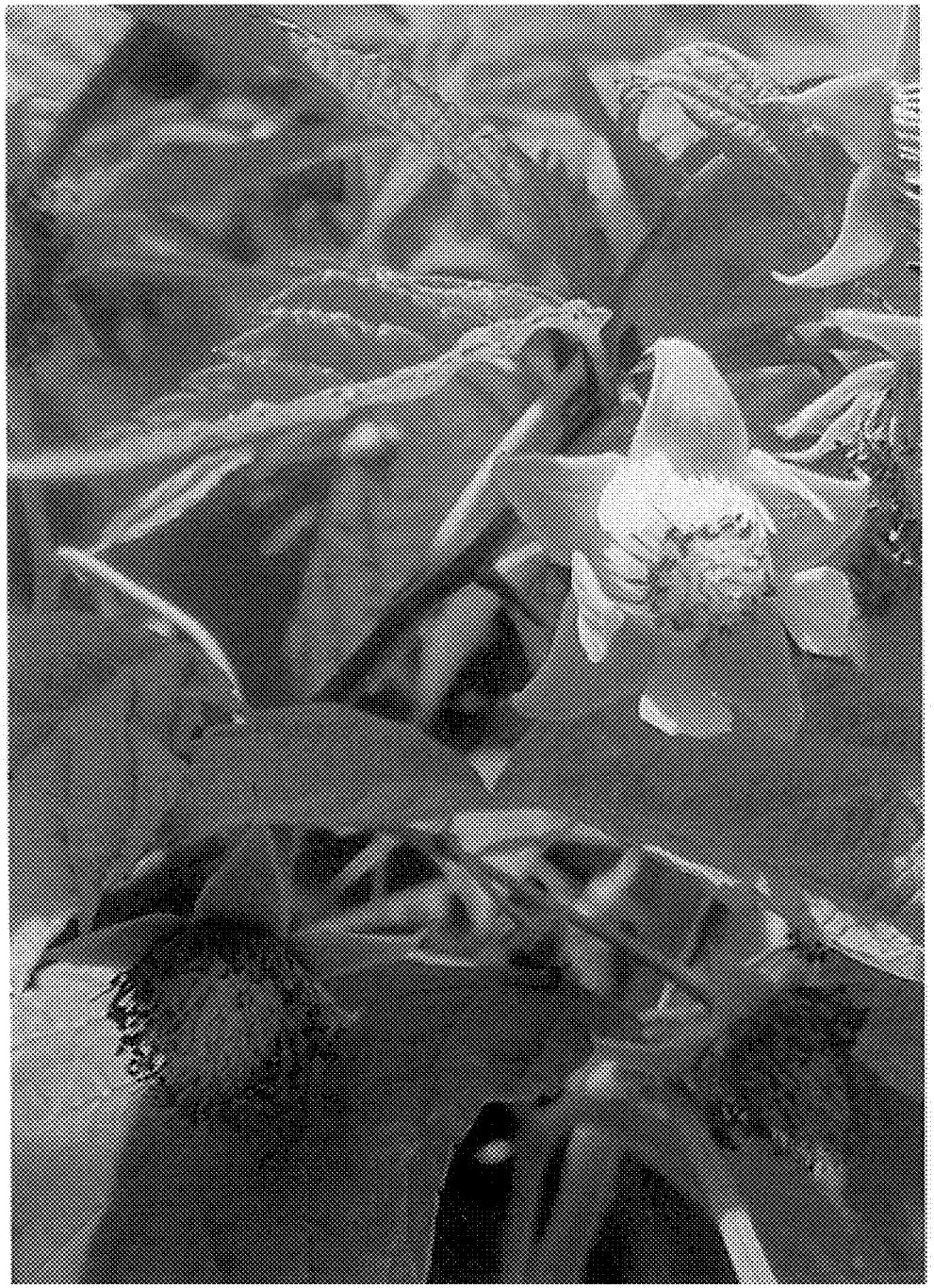
FIG. 4 is a photograph showing a flower and immature fruit of WSU 1090.

The lateral length, number of nodes, number of flowers, flower diameter and color are given in Table 4. Although variable from year to year and among locations, May 27, 2001 was the date for the first open flowers at Puyallup, Wash., three days before 'Meeker'. The date of the peak bloom was Jun. 9, 2001, two days before 'Meeker'. Flower morphology is typical of most red raspberry cultivars and is not useful to identify WSU 1090 (FIG. 4). The petals are White Group (155A), sepals Yellow-Green Group (147C)

and pedicels Greyed-Purple Group (184A). The flowers are perfect with generally 5 sepals, 5 petals and numerous stamens and pistils. Occasionally (approximately 10%) flowers had 6 petals. The flowering trusses are cymose in elongate clusters and at each node on the fruiting lateral the flowers are predominantly borne singly, or sometimes in clusters of two or more. The flowers have no discernable fragrance. The pedicel length, number of fruit and number of fruiting nodes are given in Table 5. The pedicel length and number of fruit per lateral were similar in WSU 1090 and 'Meeker' and greater than for 'Tulameen'. Differences between the number of flowers (Table 4) and number of fruit (Table 5) are within sampling errors.

A plant of WSU 1090 was moved into the greenhouse in spring had some open flowers one April 28th morning and some additional flower traits were measured. The number of stamens per flower was counted on the two flowers that were open. One had 66 stamens and the other had 75 for an average of 70.5. The number of stigma were not counted, but they should be similar to the number of drupelets per fruit (Table 6 reports this as 133.6 druplets/fruit). The color of the anther portion of the stamen was 158A and the filaments were 155D. The color of the stigma was 157B. The color designations are according to The Royal Horticulture Society Colour Chart.

Figure 5:
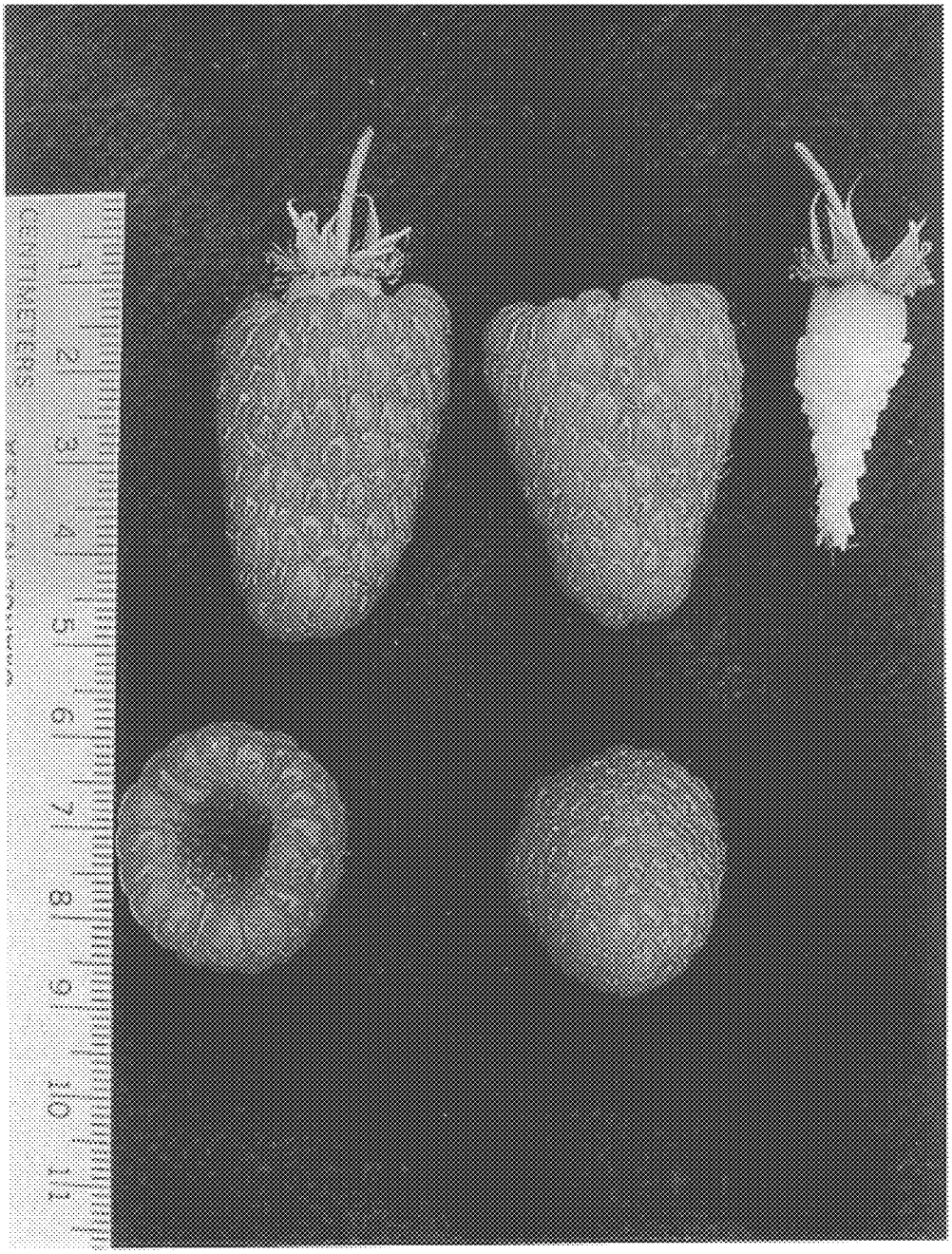
FIG. 5 is a photograph of fruit and receptacle of WSU 1090.

Fruit morphological characteristics are given in Table 6. Fruit is conic in shape and glossy (FIG. 5). Fruit of WSU 1090 has a traditional red raspberry flavor. Fruit production has not been observed on primocanes. The pH, titratable acidity, soluble solids and anthocyanin concentration of processing ripe fruit are given in Table 7. Soluble solids content of WSU 1090 did not differ from 'Meeker' or 'Tulameen' and titratable acidity was similar to 'Meeker' and less than 'Tulameen'. The flavor of WSU 1090 is somewhat similar to 'Chilliwack'.

Fruit was also harvested at a fresh market stage and stored at 4° C. for 8 days and then 20° C. for 4 hours (Table 8). Fruit at the fresh market stage was much lighter in color and more yellow than at processing ripe fruit. Fruit darkened and softened during storage, but did not differ greatly from 'Tulameen' in color. Fruit was much firmer than 'Tulameen' and was judged to remain acceptable after storage. Fruit of WSU 1090 was similar to 'Tulameen' in color at harvest, and after storage. Fruit of WSU 1090 was much firmer at harvest and after storage than 'Tulameen'. Fruit firmness of WSU 1090 after storage was similar to firmness of 'Tulameen' at harvest. Based on color and firmness after storage, WSU 1090 should store acceptably for fresh market use. Fruit firmness was measured as the force in grams required to close the fruit opening.

Fruit production was measured in replicated plots at Puyallup and Mt. Vernon (Table 9). Yield for WSU 1090 was similar to 'Tulameen' and 'Meeker' and greater than for 'Willamette' (non-patented). Fruit weight averaged over the season was 5.0 g and very firm (203 g). The midpoint of harvest was July 17, two days after 'Meeker' and 'Tulameen' and 9 days after 'Willamette'.

Disease Resistance

WSU 1090 is susceptible to the large raspberry aphid (*Amphorophora agathonica*) the vector for the mosaic virus complex. It is susceptible to raspberry bushy dwarf virus (RBDV) via pollen transmission. In some years this variety has shown high levels of fruit rot (primarily *Botrytis cinera*) in unsprayed plots, but when observed for several years, did not differ significantly from other cultivars (Table 9). In unsprayed plots, the canes had a low incidence of anthracnose and cane botrytis and moderate incidence of spur blight.

TABLE 1

Cane measurements taken Jul. 24, 2001, Farm 5, Puyallup, WA

| | Primocane measurements | | | | |
|---|---|---|---|---|---|
| | Number of canes | Diameter (cm) at base | Diameter (cm) at 4 ft | Cane length (cm) | No. of nodes |
| WSU 1090 | 34.7 a | 1.39 a | 1.43 a | 240 a | 41.3 a |
| Meeker | 34.3 a | 1.04 b | 1.17 a | 230 a | 44.3 a |
| Tulameen | 27.0 a | 1.02 b | 0.94 a | 182 b | 38.3 a |

| | Internode length (cm) | Cane color RHS[z] | Spine color RHS |
|---|---|---|---|
| WSU 1090 | 7.5 a | 145B | 71A |
| Meeker | 7.8 a | 145A | 75A |
| Tulameen | 6.2 a | 144B | 71A |

| | Floricane measurements | | | |
|---|---|---|---|---|
| | Diameter (cm) at base | Diameter (cm) at 4 ft | Cane length (cm) | No. of nodes |
| WSU 1090 | 1.84 a | 1.30 a | 188 a | 28.7 b |
| Meeker | 1.40 a | 0.65 b | 162 ab | 30.0 b |
| Tulameen | 0.97 a | 0.67 b | 155 b | 47.0 a |

| | Internode length (cm) | Lateral length (cm) | Cane color RHS | Plot height (cm) | Plot width (cm) |
|---|---|---|---|---|---|
| WSU 1090 | 10.0 a | 84 a | 165B | 213 | 158 |
| Meeker | 6.4 a | 75 a | 165B | 168 | 145 |
| Tulameen | 2.9 a | 56 b | 166C | 145 | 114 |

Three canes were measured for each clone.
Internode and lateral length measured at 4 ft.
[z]The Royal Horticultural Society Colour Chart designations
Values not followed by the same lower case letter are significantly different, $p < 0.05$.

TABLE 2

Primocane leaves measured at 4 feet on Jul. 24, 2001, Farm 5, Puyallup, WA.

| | WSU 1090 | Meeker | Tulameen |
|---|---|---|---|
| No. leaflets | 5 a | 5 a | 5 a |
| stipules length (mm) | 3.4 a | 6.2 a | 4.6 a |
| Petiole length (cm) | 9.6 a | 10.4 a | 7.2 b |
| Rachis length (cm) | 4.9 a | 4.3 ab | 3.9 b |
| Terminal leaflet | | | |
| Length (cm) | 13.0 a | 11.5 ab | 11.1 b |
| Width (cm) | 8.6 a | 7.1 b | 6.6 b |
| Petiolule length (cm) | 2.2 a | 1.0 a | 1.2 a |
| Distal lateral leaflet | | | |
| Length (cm) | 9.9 a | 8.4 b | 7.8 b |
| Width (cm) | 5.2 a | 3.9 b | 3.6 b |
| Petiolule length (mm) | 0 a | 0 a | 0 a |
| Basal lateral leaflet | | | |
| Length (cm) | 13.1 a | 11.0 b | 9.2 c |
| Width (cm) | 8.7 a | 7.0 b | 5.7 c |
| Petiolule length (mm) | 1.4 a | 5.8 a | 4.0 a |

TABLE 2-continued

Primocane leaves measured at 4 feet on Jul. 24, 2001, Farm 5, Puyallup, WA.

| | WSU 1090 | Meeker | Tulameen |
|---|---|---|---|
| Leaf color | | | |
| Upper surface Munsell | 7.5GY 3/2 | 7.5GY 3/3 | 7.5GY 4/3 |
| Lower surface Munsell | 5GY 5/2 | 5GY 5/2 | 5GY 6/2 |

Five leaves were measured for each clone.
Values not followed by the same lower case letter are significantly different, $p < 0.05$.

TABLE 3

Floricane leaves measured at 4 feet on Jul. 24, 2001, Farm 5, Puyallup, WA

| | WSU 1090 | Meeker | Tulameen |
|---|---|---|---|
| No. leaflets | 3 | 3 | 3 |
| Petiole length (cm) | 7.4 a | 7.14 a | 5.7 b |
| Stipules length (mm) | 3.2 b | 5.6 a | 2.76 b |
| Terminal leaflet | | | |
| Length (cm) | 9.7 ab | 11.1 a | 7.8 b |
| Width (cm) | 8.3 a | 8.0 a | 6.7 b |
| Petiolule length (cm) | 2.7 a | 3.3 a | 2.9 a |
| Basal leaflet | | | |
| Length (cm) | 8.8 a | 9.4 a | 7.3 b |
| Width (cm) | 4.9 b | 5.8 a | 4.4 b |
| Petiolule length (mm) | 1.4 b | 4.0 a | 2.2 b |
| Color | | | |
| Upper surface of leaf Munsell | 7.5 GY 3/3 | 7.5 GY 3/3 | 7.5 GY 3/3 |
| Lower surface of leaf Munsell | 5 GY 5/2 | 5 GY 5/2 | 5 GY 5/2 |

Five leaves were measured for each clone.
Values not followed by the same lower case letter are significantly different, $p < 0.05$.

TABLE 4

Flower data collected Jun. 14, 2001 Farm 5, Puyallup, WA

| | flower diameter | | | | |
|---|---|---|---|---|---|
| | sepal to sepal (cm) | petal to petal (cm) | No. of flowers/lateral | No. of nodes/lateral | No. fruiting nodes |
| WSU 1090 | 2.6 a | 1.0 a | 16.3 b | 26.0 a | 11.0 a |
| Meeker | 2.3 a | 1.0 a | 37.3 a | 28.3 a | 15.0 a |
| Tulameen | 2.3 a | 1.5 a | 14.7 b | 14.3 b | 9.3 a |

| | No. of flowers/fruiting node | Lateral length (cm) | Color[z] petals | sepals | pedicels |
|---|---|---|---|---|---|
| WSU 1090 | 1.5 b | 79.8 a | 155A | 147C | 184A |
| Meeker | 2.5 a | 69.4 ab | 155A | 194B | 184A |
| Tulameen | 1.6 b | 48.1 b | 155C | 194B | 183B |

Three flowering laterals were measured at four feet high on the cane for each clone.
[z]The Royal Horticultural Society Colour Chart designations
Values not followed by the same lower case letter are significantly different, $p < 0.05$.

TABLE 5

Lateral measurements taken at 4 feet on Jul. 24, 2001, Farm 5, Puyallup, WA

| | Pedicel length (cm) | Number of fruit | Number of fruiting nodes | Number of fruit/node |
|---|---|---|---|---|
| WSU 1090 | 3.4 a | 22.7 a | 11.0 a | 2.1 a |
| Meeker | 3.1 a | 23.3 a | 11.0 a | 2.1 a |
| Tulameen | 2.0 b | 13.3 b | 8.0 a | 1.6 a |

Three fruiting laterals were measured at four feet high on the cane for each clone.
Values not followed by the same lower case letter are significantly different, $p < 0.05$.

TABLE 6

Fruit morphological characteristics, fruit harvested Jul. 6, 2001, Farm 5, Puyallup, WA.

| | WSU 1090 | Meeker | Tula-meen | Chilli-wack | WSU 994 |
|---|---|---|---|---|---|
| length (cm) | 3.29 a | 2.07 d | 2.59 c | 2.13 d | 2.80 b |
| width (cm) | 2.41 a | 2.05 c | 2.18 b | 1.92 d | 2.06 c |
| Length/width | 1.37 a | 1.01 d | 1.19 b | 1.11 c | 1.36 a |
| Diameter of receptacle (cm) | 0.98 a | 0.90 b | 0.91 ab | 0.84 b | 0.90 b |
| Length of receptacle (cm) | 2.78 a | 1.47 d | 2.26 b | 1.70 d | 2.29 b |
| No. drupelets | 133.6 a | 75.2 d | 87.1 c | 74.0 d | 119.0 b |
| Fruit weight (g) | 8.36 a | 4.26 c | 5.48 b | 3.55 d | 5.43 b |
| Drupelet weight (mg) | 62.7 a | 58.6 a | 63.0 a | 48.1 b | 47.1 b |
| Drupelet length (mm) | 5.5 a | 5.0 cd | 5.4 ab | 4.6 c | 5.1 bc |
| Drupelet width (mm) | 4.2 a | 3.7 a | 4.0 a | 3.8 a | 3.6 a |
| Seed weight/fruit (g) | 0.29 a | 0.15 c | 0.18 b | 0.16 c | 0.20 b |
| Individual seed wt (mg) | 2.16 a | 1.99 a | 2.09 a | 2.10 ab | 1.72 b |
| Color (Munsell) | 2.5R 3/4 | 2.5R 3/6 | 2.5R 3/6 | 2.5R 3/6 | 2.5R 3/7 |

Ten fruit were measured for each clone.
Values not followed by the same lower case letter are significantly different, $p < 0.05$.

TABLE 7

Analysis of raspberry fruit harvested July 2000, Farm 5, Puyallup, WA.

| | pH | Titratable acidity (% citric acid) | Soluble solids (%) | Anthocyanins (mg/g fruit) |
|---|---|---|---|---|
| WSU 1090 | 2.98 b | 1.18 b | 10.4 a | 0.440 b |
| Meeker | 3.18 a | 1.05 b | 11.8 a | 0.468 b |
| Tulameen | 3.00 b | 1.48 a | 11.3 a | 0.406 b |
| Willamette | 2.96 b | 1.52 a | 11.4 a | 0.748 a |

Analysis of three replications of 10 g of fruit.
Values not followed by the same lower case letter are significantly different, $p < 0.05$.

TABLE 8

Storage of fruit harvested Jul. 16, 2001, Farm 5, Puyallup, WA

| | Fruit characteristics prior to storage | | Fruit characteristics after storage | |
|---|---|---|---|---|
| | Firmness (g) | Munsell color designation | Firmness (g) | Munsell color designation |
| WSU 1090 | 364 a | 5R 3/7 | 238 a | 2.5R 3/5 |
| Tulameen | 234 b | 5R 3/6 | 138 b | 2.5R 3/5 |

Thirteen fruit measured for each clone on each date.
Fruit stored 8 days at 4 C., then room temperature (20 C.) for 4 hours.
Values not followed by the same lower case letter are significantly different, $p < 0.05$.

TABLE 9

Combined harvest data from six harvest seasons.

| | Yield (t/a) | Fruit rot (%) | Fruit wt. (g) | Fruit firmness (g) |
|---|---|---|---|---|
| WSU 1090 | 7.8 a | 9.8 a | 5.0 a | 203 a |
| Tulameen | 7.8 a | 5.6 a | 4.3 b | 174 c |
| Meeker | 7.1 a | 5.9 a | 3.3 c | 180 b |
| Willamette | 5.8 b | 5.1 a | 3.2 c | 180 bc |

TABLE 9-continued

Combined harvest data from six harvest seasons.

| | Harvest season | | | |
|---|---|---|---|---|
| | 5% harvest | 50% harvest | 95% harvest | Length of season (days) |
| WSU 1090 | 7/5 a | 7/17 a | 7/29 a | 24 b |
| Tulameen | 7/3 a | 7/15 a | 7/30 a | 28 a |
| Meeker | 7/3 a | 7/15 a | 7/28 a | 26 ab |
| Willamette | 6/27 b | 7/8 b | 7/21 b | 23 b |

Based on harvest of three replications of three plants for each location or harvest season.
1995 harvest of 1993 planted raspberries, Puyallup, WA
1996 harvest of 1993 planted raspberries, Puyallup, WA
1999 harvest of 1997 planted raspberries, Puyallup, WA
2000 harvest of 1997 planted raspberries, Puyallup, WA
2000 harvest of 1998 planted raspberries, Mt. Vernon, WA
2001 harvest of 1998 planted raspberries, Puyallup, WA
Firmness not measured in 1996 harvest and at Mt. Vernon.
Values not followed by the same lower case letter are significantly different, $p < 0.05$.

I claim:

1. A new and distinct variety of raspberry plant, as illustrated and described herein.

* * * * *